United States Patent
Rodriguez

(10) Patent No.: US 6,319,911 B1
(45) Date of Patent: *Nov. 20, 2001

(54) PREVENTION OF OVARIAN CANCER BY ADMINISTRATION OF PROGESTIN PRODUCTS

(75) Inventor: Gustavo C. Rodriguez, Durham, NC (US)

(73) Assignee: New Life Pharmaceuticals Inc., Chicago, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/118,143

(22) Filed: Jul. 16, 1998

Related U.S. Application Data

(63) Continuation-in-part of application No. 08/713,834, filed on Sep. 13, 1996.

(51) Int. Cl.$^7$ .................................................. A61K 31/56
(52) U.S. Cl. ............................................................ 514/170
(58) Field of Search ............................................. 514/170

(56) References Cited

U.S. PATENT DOCUMENTS

| | | | |
|---|---|---|---|
| 4,594,340 | 6/1986 | Partridge et al. | 514/167 |
| 4,757,061 | 7/1988 | Faustini et al. | 514/177 |
| 4,760,053 | 7/1988 | Labrie | 514/15 |
| 4,800,198 | 1/1989 | DeLuca et al. | 514/167 |
| 4,808,578 | 2/1989 | Faustini et al. | 514/177 |
| 4,808,616 | 2/1989 | Buzzetti et al. | 514/177 |
| 4,814,327 | 3/1989 | Ottow et al. | 514/179 |
| 4,840,943 | 6/1989 | Buzzetti et al. | 514/177 |
| 4,855,305 * | 8/1989 | Cohen | 514/171 |
| 4,870,069 | 9/1989 | Ottow et al. | 514/179 |
| 4,904,650 | 2/1990 | Buzzetti et al. | 514/177 |
| 4,954,790 | 9/1990 | Barber | 332/164 |
| 5,006,518 | 4/1991 | Moguilewsky | 514/179 |
| 5,081,114 | 1/1992 | Gourvest et al. | 514/177 |
| 5,086,047 | 2/1992 | Gourvest et al | 514/177 |
| 5,089,488 | 2/1992 | Ottow et al. | 514/179 |
| 5,190,935 | 3/1993 | Binderup et al. | 514/167 |
| 5,206,229 | 4/1993 | Calverly et al. | 514/167 |
| 5,227,375 | 7/1993 | Labrie et al. | 514/172 |
| 5,246,925 | 9/1993 | DeLuca et al. | 514/167 |
| 5,278,155 | 1/1994 | Ikekawa et al. | 514/167 |
| 5,362,720 | 11/1994 | Labrie | 514/169 |
| 5,364,847 | 11/1994 | Labrie et al. | 514/182 |
| 5,373,004 | 12/1994 | DeLuca et al. | 514/167 |
| 5,374,629 | 12/1994 | Calverley et al. | 514/167 |
| 5,380,720 | 1/1995 | DeLuca et al. | 514/167 |
| 5,387,582 | 2/1995 | Hansen | 514/167 |
| 5,389,622 | 2/1995 | Posner et al. | 514/167 |
| 5,401,731 | 3/1995 | Calverley et al. | 514/167 |
| 5,411,949 | 5/1995 | Neef et al. | 514/167 |
| 5,428,029 | 6/1995 | Doran et al. | 514/167 |
| 5,434,146 | 7/1995 | Labrie et al. | 514/169 |
| 5,446,035 | 8/1995 | Neef et al. | 514/167 |
| 5,451,574 | 9/1995 | Baggiolini et al. | 514/167 |
| 5,461,041 | 10/1995 | Bergink et al. | 514/179 |
| 5,484,782 | 1/1996 | DeLuca et al. | 514/167 |
| 5,486,511 | 1/1996 | Weintraub et al. | 514/178 |
| 5,496,813 | 3/1996 | Eugster et al. | 514/172 |
| 5,502,044 | 3/1996 | Buzzetti et al. | 514/177 |
| 5,512,554 | 4/1996 | Baggiolini et al. | 514/167 |
| 5,532,228 | 7/1996 | Neef et al. | 514/167 |
| 5,536,713 | 7/1996 | DeLuca et al. | 514/167 |
| 5,547,947 | 8/1996 | Dore et al. | 514/167 |
| 5,554,599 | 9/1996 | GrueSorenen et al. | 514/167 |
| 5,583,129 * | 12/1996 | Spona et al. | 514/178 |

FOREIGN PATENT DOCUMENTS

WO 98/10771   3/1998   (WO) .

OTHER PUBLICATIONS

Allgood, V.E. et al. "Analysis of chicken progesterone receptor function and phosphorylation using an adenovirus–mediated procedure for high–efficiency DNA transfer," *Biochemistry*, 36(1):224–232 (1997).

Arends, M.J. et al. "Apoptosis: Mechanisms and roles in pathology," *Int. Rev. Exp. Pathol.*, 32:223–254 (1991).

Arrick, B.A. et al. "Differential regulation of three transforming growth factor b species in human breast cancer cell lines by estradiol," *Cancer Res.*, 50:299–303 (1990).

Bai, W. et al. "Differential phosphorylation of chicken progesterone receptor in hormone–dependent and Ligand–independent activation," *J. Biol. Chem.*, 272(16):10457–10463 (1997).

Bates, R.C. et al. "Involvement of integrins in cell survival," *Cancer Metastasis Rev*, 14(3):191–203 (1995).

Berchuck, A. et al., "Regulation of growth of normal ovarian epithelial cells and ovarian cancer cell lines by transforming growth, factor–β," *Am. J. Obstet. Gynecol.*, 166:676–84 (1992).

Berchuck, A. et al., "The role of peptide growth factors in epithelial ovarian cancer," *Obstet. Gynecol.*, 75:255–62 (1990).

Brenner, R.M. et al., "Cyclic changes in the primate oviduct and endometrium. In: *The Physiology of reproduction,*" Knobil, E. et al., (eds.), New York: Raven Press, pp. 541–569 (1994).

Bu, S.Z. et al., "Progesterone induces apoptosis and up–regulation of p53 expression in human ovarian carcinoma cell lines," *Cancer*, 79: 1944–1950 (1997).

(List continued on next page.)

*Primary Examiner*—Jerome D. Goldberg
(74) *Attorney, Agent, or Firm*—Raymond N. Nimrod

(57) ABSTRACT

The present invention relates to methods for preventing the development of epithelial ovarian cancer by administering progestin products, either alone or in combination with other agents such as estrogen products.

19 Claims, No Drawings

OTHER PUBLICATIONS

Bundesverband der Pharmazeutishen Industrie, "Rote liste 1995," Ecv. Editio Cantor, *Aulendorf*(DE), pp. 75023–75024 (1995).

Chan, L.N. et al., "N–(4–hydroxyphenyl) retinamide prevents development of Tlymphomas in AKR/J mice," *Anticancer Research, 17:*499–503 (1997).

Cohen, J.J., "Apoptosis," *Immun. Today, 14:*126–130 (1993).

Delia, D. et al., "N–(4–hydroxyphenyl) retinamide induces apoptosis of malignant hemopoietic cell lines including those unresponsive to retinoic acid," *Cancer Res., 53(24)*:603641 (1993).

Eguchi, Y. et al., "Isolation and characterization of the chicken bcl–2 gene: expression in a variety of tissues including lymphoid and neuronal organs in adult and embryo," *Nucleic Acids Research, 20(16)*:4187–41922 (1992).

el–Bayoumy, K. et al., "Chemo prevention of cancer by organoselenium compounds," *J. Cell. Biochem, Suppl., 22:*92–100 (1995).

Ellis, R. et al., "Mechanisms of cell death," *Ann. Rev. Cell. Bio., 17:*663–698 (1991).

Evans, D.L. et al., "Molecular evolution and secondary structural conservation in the B–cell lymphoma leukemia 2 (bcl–2) family of proto–oncogene products,"*J. Mol. Evol., 41(6)*:775–83 (1995).

Fredrickson, T.N. et al., "Ovarian tumors of the hen," *Environ Health Perspect, 73:*35–51 (1987).

Gentry, L.E. et al., "Type I transforming growth factor–beta: Amplified expression and secretion of mature and precursor polypeptides in Chinese hamster ovary cells," *Mol. Cell. Biol., 7:*3418–27 (1987).

Grimes et al., "Primary Prevention of Gynecologic Cancers," *Am. J. Obstetrics and Gynecology, 172(1):*227–235 (1995).

Havrilesky, L.J. et al., "Regulation of Apoptosis in Normal and Malignant Ovarian Epithelial Cells by Transforming Growth Factor β," *Cancer Research, 55:*944–948 (Feb. 15, 1995).

Hickey, M.J. et al., "Metabolic and Endocrinologic Effects of Steroidal Contraception Obstetrics, " Ch 24, J. Sciarra, Editor, 1996 revised edition, Lippincott, Philadelphia, pp. 1–14 (1996).

Hotchkiss, J. et al., "The menstrual cycle and its neuroendocrine control," In: *The Physiology of Reproduction,* Knobil, E. et al. (eds.), New York: Raven Press, pp. 711–736 (1994).

Hurteau, J.A. et al., "Transforming growth factor–β inhibits proliferation of human ovarian cancer cells obtained from ascites," *Cancer, 74:*93–99 (1994).

Johnson, A.J. et al., "Expression of bcl–2 and nr–13 in hen ovarian Follicles during development," *Biol. Repro., 57:*1097–1103 (1997).

Kaiserman–Abramof, I. et al., "Ultrastructural epithelial conation of the primate endometrium. (rhesus monkey)," *Am. J. Anat.,* pp. 13–30 (1989).

Lingeman, C.H., "Etiology of cancer of the human ovary," A review, *J. Natl. Cancer Inst., 53:*1603–1618 (1974).

Lotan, R., "Retinoids in cancer chemo prevention," [Review] *FASEB J., 10(9):*1031–9, (1996).

Lumbiganon, P., "Depot–medroxyprogesterone acetate (DMPA) and cancer of the endometrium and ovary," *Contraception, 49:*203–209 (Mar., 1994).

Mulheron, G.W. et al., "Rat thecal/interstitial cells express transforming growth factor–beta type 1 and 2 is regulated by gonadotropin in vitro," *Endocrin, 129:*368–3 73 (1991).

Mulheron, G.W. et al., "Rat granulosa cells express transforming growth factor–beta type 2 messenger ribonucleic acid which is regulatable by fillide stimulating hormone in vitro," *Endocrin, 126:*1771–1779 (1990).

Mutch, D.G. et al., "Biology of epithelial ovarian cancer," *Clin. Obstet. Gynecol., 37:*406–422 (1994).

O'Brien, V. et al., "Expression of the integrin alpha 5 subunit in HT29 colon carcinoma cells suppresses apoptosis triggered by serum deprivation," *Ex. Cell. Res., 224(1)*:208–213 (1996).

Oberhammer, F.A. et al., "Induction of apoptosis in cultured hepatocytes and in regressing liver by transforming growth factor–β1," *Proc. Natl. Acad. Sci. USA, 89:*5408–5412 (1992).

Oridate, N. et al., "Inhibition of proliferation and induction of apoptosis in cervical carcinoma cells by retinoids: implications for chemo prevention," *J. Cell. Biochem., Suppl, 23:*80–6 (1995).

Pascale, R.M. et al., "Chemoprevention by S–adenosyl–L–methionine of rat liver carcinogenesis initiated by 1,2–dimethylhydrazine and promosted by orotic acid," *Carcinogenesis 16(2)*:427–30 (1995).

Pfleiderer, "die Problematik einer prophylaktischen Chemotherapie, einer der Remission bei der Therapie des Ovarialkarzinoms," *Geburtsh. u. Frauenheilk, 36(2)*:132–139 (1976).

Physician's Desk Reference 1996, Product Information, pp. 1871–1876 2136–2138 2601–2604 2759–2762 and 2813–2818 (1996).

Ponzoni, M. et al., "Differential effects of N–(4–hydroxyphenyl) retinamide and retinoic acid on neuroblastoma cells: apoptosis versus differentiation," *Can. Res., 55(4)*:853–61 (1995).

Qin, S. et al., "Cooperation of tyrosine kinases p72syk and p53/56lyn regulates calcium mobilization in chicken B cell oxidant stress signaling," *Eur. J. Biochem, 236(2)*:443–9 (1996).

Rampalli, A.M. et al., "Insulin regulates expression of c–fos and c–jun and suppresses apoptosis of lens epithelial cells," *Cell. Growth Differ., 6(8)*:945–53 (1995).

Reddy, B.S. et al., "Chemo prevention of colon carcinogenesis by dietary perillyl alcohol," *Cancer Res., 57(3)*:420–5 (1997).

Roberts, A.B. et al., "Mechanistic interrelationships between two superfamilies: The steroid/retinoid receptors and transforming growth factor–β," In: Cancer Surveys, vol. 14; Growth Regulation hy Nuclear Hormone Receptors, *Imperial Cancer Research Fund,* pp. 205–217 (1992).

Rodriguez, G.C. et al., "Epidermal growth factor receptor expression in normal ovarian epithelium and ovarian cancer.II. Relationship between receptor expression and response to epidermal growth factor," *Am. J. Obstet. Gynecol., 164:*745–750 (1991).

Rotello, R.J. et al., "Coordinated regulation of apoptosis and cell proliferation by transforming growth factor–β1 in cultured uterine epithelial cells," *Proc. Natl. Acad. Sci. USA. 88:*3412–3415 (1991).

Rudel, H.W., "Pharmacology of Contraceptive Steroids," Chapter 19, In: Gynecology –and Obstetrics J. Sciarra, Editor, 1996 revised edition, Lippincott, Philadelphia, pp. 1–6 (1996).

Sankaranarayanan, R. et al., "Retinoids as cancer–preventive agents," [Review] IARC *Sci. Publ.,* (*139*):47–59 (1996.).

Schildkraut, J.M. et al., "Relationship Between Lifetime Ovulatory Cycles and Overexpression of Mutant p53 in Epithelial Ovarian Cancer," *J. National Cancer Institute,* 89(13):932–938 (Jul. 2, 1997).

Scott, J.S., "How to induce ovarian cancer: and how not to," *British Medical J.,* 289:781–784 (Sep. 29, 1984).

Seewaldt, V.L. et al., "All–trans–retinoic acid mediated GI arrest but not apoptosis of normal human mammary epithelial cells," *Cell Growth Differ.,* 6(7):863–9 (1995).

Syvala, H. et al., "Expression of the chicken progesterone receptor forms A and B is differentially regulated by estrogen in vivo," *Biochemical and Biophysical Research Communications,* 231:537–576 (1997).

Taetle, R. et al., "Effects of transforming growth factor–β1 on growth and apoptosis of human acute myelogenous leukemia cells," *Cancer Research,* 53:3386–3393 (1993).

Takayama S. et al., "Evolutionary conservation of function among mammalian, avain, and viral homologs of the bcl–2 oncoprotein," *DNA Cell. Biol.,* 13(7):679–92 (1994).

Thompson, H.J. et al., "Sulfone metabolite of sulindac; inhibits mammary carcinogenesis," *Cancer Res.,* 57(2):267–71 (1997).

Thompson, H.J. et al., "Ip C. Comparison of the effects of an organic and an inorganic form of selenium on a mammary carcinoma cell line," *Carcinogenesis* 15(2):183–6 (1994).

Toma, S. et al., "Effects of al–trans–retinoic acid and 13–cis– retinoic acid on breast–cancer cell lines : growth inhibition and apoptosis induction," *Int. J. Cancer,* 70(5):619–27 (1997).

Vilgrasa, X. et al., "Differential expression of bcl–2 and bcl–x during chicken spermatogenesis," *Mol. Reprod. Dev.,* 47(1):26–9 (1997).

Wakefield, L. et al., "Regulation of transforming growth factor–β subtypes by members of the steroid hormone superfamily," *J. Cell. Sci. Suppl.,* 13:139–148 (1990).

Wijsman, J.H. et al., "A new method to detect apoptosis in paraffin sections: In situ end– labeling of fragmented DNA," *J. Histochem. Cyochem.,* 41:7–12 (1993).

Woolveridge, I. et al., "The inhibition of androstenedione production in mature thecal cells from the ovary of the domestic hen (*Gallus domesticus*): evidence for the involvement of progestins," *Steroids,* 62:214–220 (1997).

Yanagihara, K. et al., "Transforming growth factor–β1 induces apoptotic cell death in cultured human gastric carcinoma cells," *Cancer Res.,* 52:4042–4045 (1992).

PCT International Search Report; PCT/US97/16601.

Dolivet et al., "Current knowledge on the action of retinoids in carcinoma of the head and neck," [Review], *Rev. Laryngol. Otol. Rhinol.* (*Bord*) 117(1):19–26 (1996) (English abstract).

Etches et al., "Reptilian and avian follicular hierarchies: Models for the study of ovarian development," *J. Exp. Zoo, Suppl 4*:112–122 (1990).

Fukuda et al., "Induction of apoptosis by transforming growth factor–1 in the rat hepatoma cell fine McA–RH7777: A possible associate with tissue transglutaminase expression," *Hepatology,* 18:945–953 (1993).

Gould, "Cancer chemoprevention and therapy by monoterpenes," *Environ. Health Perspect.,* 105 (*Suppl 4*):977–9 (1997).

Kuo, "Antiproliferative potency of structurally distinct dietary flavonoids on human colon cancer cells," *Cancer Lett.,* 110(1–2):41–8 (1996).

Mayr et al., "Sequence of an exon of tumour suppressor p53 gene—a comparative study in domestic animals: mutation in a feline comparative study in domestic animals; mutation in a feline solid mammary carcinoma," *Br. Vet. J.,* 151(3):325–9 (1995).

Wilson "Adeno–carcinomata in hens kept in a constant environment," *Poult. Sci.,* 37:1253 (1958).

Milligan et al., "Programmed Cell Death During Development of Animals", in *Cellular Aging and Cell Death,* Wiley––Liss Inc., Holbrook et al., (Eds.), pp. 181–208 (1996).

Canman et al., "DNA Damage Responses: P–53 Induction, Cell Cycle Pertubations, and Apoptosis", *Cold Spring Harbor Symp. Quant. Biol.,* 59:277–286 (1994).

Baker et al., "Etiology, Biology, and Epidemiology of Ovarian Cancer", *Seminars in Surgical Oncology,* 10:242–248 (1994).

Amos et al., "Genetic Epidemiology of Epithelial Ovarian Cancer", *Cancer,* 71:566–572 (1993).

Wittemore, "Characteristics Relating To Ovarian Cancer Risk: Implications for Preventing and Detection," *Gynecologic Oncology,* 55:S15–S19 (1994).

Greene et al., "The Epidemiology of Ovarian Cancer", *Seminars in Oncology,* 11:209–225 (1984).

Wittemore et al., "Characteristics Relating to Ovarian Cancer Risk: Collaborative Analysis of 12 U.S. Case–Control Studies", *Am. J. Epidem.,* 136:1212–1220 (1992).

Wu et al., "Personal and Environmental Characteristics Related To Epithelial Ovarian Cancer", *Am. J. Epidem.,* 108(6):1216–1227 (1988).

Rossing et al., "Ovarian Tumors in a Cohort of Infertile Women", *New Engl. J. Med.,* 331:771–776 (1994).

Casagrande et al., "Incessant Ovulation and Ovarian Cancer," *Lancet,* pp. 170–172 (Jul. 28, 1979).

Rosenberg et al. (The WHO Collaborative Study of neoplasia and Steroid Contraceptives), "A Case Control Study of Oral Contraceptive Use and Invasive Epithelial Ovarian Cancer", *Am. J. Epidem.,* 139:654–661 (1994).

Stanford et al., "Epithelial Ovarian Cancer and Combined Oral Contraceptives", *Int'l J. Epidem.,* 18:538–545 (1989).

Lee et al., "The Reduction in Risk of Ovarian Cancer Associated with Oral Contraceptive Use", *New England J. Medicine,* 316:650–655 (1987).

Gross et al., "The Estimated Effect of Oral Contraceptives Use on the Cumulative Risk of Epithlial Ovarian Cancer", *Obstetrics Gynecology,* 83:419–424 (1994).

Franseschi et al., "Pooled Analysis of 3 European Case–Control Studies of Epithelial Ovarian Cancer: III. Oral Contraceptive Use", *Int'l J. Cancer,* 49:61–65 (1991).

Rosenblatt et al., "High–Dose and Low–Dose Combined Oral Contraceptives: Protection Against Epithelial Ovarian Cancer and The Length of the Protective Effect", *Eur. J. Cancer,* 28A:1872–1876 (1992).

Stanford et al. (The WHO Collaborative Study of Neoplasia and Steroid), "Depot–medroxyprogesterone Acetate (DMPA) and Risk of Epithelial Ovarian Cancer", *Int'l J. Cancer,* 49:191–195 (1991).

Liang et al., "Risk of Breast, Uterine Corpus, and Ovarian Cancer in Women Receiving Medroxyprogesterone Injections", *JAMA,* 249:2909–2912 (1983).

Lowe et al., "P53–Dependent Apoptosis in Tumor Progression and in Cancer Therapy", in *Cellular Aging and Cell Death*, Wiley–Liss Inc., Holbrook et al., (Eds.), pp. 209–234 (1996).

Lockshin et al., "The Biology of Cell Death and Its Relationship to Aging", in *Cellular Aging and Cell Death*, Wiley–Liss, Inc., Holbrook et al., (Eds.), pp. 167–180 (1996).

Bast et al., "Ovarian Cancer", in *Harrison's Principles of Internal Medicine*, Thirteenth Edition, Isselbacher et al., (Eds.), McGraw–Hill, New York, Chapter 321, pp. 1853–1858 and Chapter 340, pp. 2017–2036 (1994).

Rodriguez et al., "Estrogen Replacement Therapy and Fatal Ovarian Cancer", *Am. J. Epidem., 141*:828–835 (1995).

Dunn, I.C. et al., "The Effect of Photoperiodic History on Egg Laying in Dwarf Broiler Hens," In: *Physiology and Reproduction on : Poultry Science, vol. 71*, pp. 2090–2098 (1992).

Christopherson, W. A. et al., "Responsiveness of human carcinoma cells of gynecologic origin to 1,25–dihydroxycholecalciferol," *Am. J. Obstet. Gynecol., 155(6)*:1293–1296 (1986).

Moore, T.B. et al., "Differentiating Effects of 1,25–Dihydroxycholecalciferol ($D_3$) on LA–N–5 Human Neuroblastoma Cells and its Synergy with Retinoic Acid," *Journal of Pediatric Hematology/Oncology, 17(4)*:311–317 (Nov., 1995).

Rustin, G.J.S. et al., "Trial of isotretinoin and calcitriol monitored by CA 125 in patients with ovarian cancer," *British Journal of Cancer, 74(9)*:1479–1481 (1996).

Saunders D.E. et al., Repression of c–myc Expression in Ovarian Carcinoma Cells by 1,25 Dihydroxyvitamin $D_3$, *Twenty–Third Annual Meeting of the Society of Gynecologic Oncologists, Mar. 15–18, 1992. Gynecol. Oncol., 45(1)*:83–84 (1992) (Abstract).

Saunders, D.E. et al., "Receptors for 1,25–Dihydroxyvitamin $D_3$ in Gynecologic Neoplasms," *Gynecologic Oncology 44(2)*:131–136 (1992).

Saunders, D.E. et al., "Nonreproductive Hormones as Biologic Modifiers in Ovarian Carcinomas," *Twenty–Fourth Annual Meeting of the Society of Gynecologic Oncologists, Feb. 7–10, 1993. Gynecol. Oncol., 49(1)*:118 (1993) (Abstract).

Saunders, D.E. et al., "Inhibition of c–myc in breast and ovarian carcinoma cells by 1,25–dihydroxyvitamin $D_3$, retinoic acid and dexamethasone," *Anti–Cancer Drugs, 4(2)*:201–208 (1993).

Saunders, D.E. et al., "Inhibition of breast and ovarian carcinoma cell growth by 1,25–dihydroxyvitamin $D_3$ combined with retonic acid or dexamethasone," *Anti–Cancer Drugs, 6(4)*:562–569 (1995).

Corder, E.H. et al., "Vitamin D and Protstate Cancer: A Prediagnostic Study with Stored Sera," *Cancer Epidemiology Biomarkers & Prevention, 2*:467–472 (1993).

Santiso–Mere et al., "Positive Regulation of the Vitamin D Receptor by Its Cognate Ligand in Heterolngous Expression Systems", *Molecular Endocrinology, 7(7)*:833–839 (1993).

Davoodi et al., "Modulation of Vitamin D Receptor and Estrogen Receptor by 1,25 $(OH)^2$–Vitamin $D^3$ in T–47D Human Breast Cancer Cells," *J. Steroid Biochem. Molec. Biol., 54(3/4)*:147–153 (1995).

Colston et al., "1,25–Dihydroxyvitamin D3and malignant Melanoma: The Presence of Receptors and Inhibition of Cell Growth in Culture," *Endocrinology, 108:*1083–1086 (1981).

Sato et al., "Antitumor Effect of $1\alpha$–Hydroxyvitamin D3," *Tohoku J. Exp. Med., 138:*445–446 (1982).

Eisman et al., Suppression of inVivo Growth of Human Cancer Solid Tumor Xenografts by 1,25–Dihydroxyvitamin D3, *Cancer Research, 47:*21–25 (1987).

Dokoh et al., Influence of 1,25–Dihydroxyvitamin D3 on Cultured Osteogenic Sarcoma Cells: Correlation with the 1,25–Dihydroxyvitamin D3 Receptor, *Cancer Research, 44:*2203–2109 (1984).

Mangelsdorf et al., "1,25–Dihydroxyvitamin D3–induced Defferentiation in a Human Promyelocytic Leukemia Cell Line (HL–60): Receptor Mediated Maturation to Macrophage–like Cells," *J. Cell. Biol., 98:*391–398 (1984).

Chida et al., "Inhibition of Tumor in Mouse Skin by $1\alpha$, 25–Dihydroxyvitamin $D3^1$," *Cancer Research, 45:*5426–5430 (1985).

Oikawa et al., Antitumor effect of 22–oxa–$1\alpha$,25–dihydroxyvitamin D3 a potent angiogenesis inhibitor, on rat mammary tumors induced by 7,12–dimethylbenz[a]anthracene, *Anti–Cancer Drugs, 2:*475–480 (1991).

Frampton et al., "Inhibition of Human Cancer Cell Growth by 1,25–Dihydroxyvitamin D3 Metabolites[1]," *Cancer Research, 43:*4443–4447 (1983).

Sporn, M.B. et al., "Prevention of Carciogenesis with Vitamin D Analogs," *Proceedings American Association for Cancer Research, No. 34, Abstracts 622* (Mar., 1993).

Saunders et al., "Additive Inhibition of RL95–2 Endometrial Carcinoma Cell Growth by Carboplatin and 1,25 Dihydroxyvitamin D3," *Gynecologic Oncology, 51:*155–159 (1993).

Welsh, J., "Induction of apoptosis in breast cancer cells in response to Vitamin D and antiestrogens," *Biochem. Cell. Biol., 72:*537–545 (1994).

Narvaez et al., "Characterization of a vitamin D3–Resistant MCF–7 Cell Line," *Endocrinology, 137(2)*:400–409 (1996).

Lefkowtiz et al., Sunlight, Vitamin D, and Ovarian Cancer Mortality Rates in W.S. Women, *International Journal of Epidemiology, 23(6)*:1133–1136 (1994).

Studzinski et al., "Sunlight–Can it Prevent as well as Cause Cancer?" *Cancer Research, 55:*4014–4022 (1995).

Speroff et al., "Steroid Contraception," in *Clinical Gynecologic Endocrinology and Infertility*, Chapter 15, Fourth Edition, pp. 461–498 (1989).

Hammond, "Climateric," *Danforth's Obstetrics and Gynecology*, Chapter 42, Seventh Edition, pp. 771–790 (1994).

Young, "Gynecologic Malignancies, Ovarian Cancer," *Harrison's Principles of Internal Medicine*, Thirteenth Edition, pp. 605–608 (1994).

Ravin, L.J. et al, *Remington's Pharmaceutical Sciences*, 18th Ed., Chpts., 75–92 (1990, Mack Publishing Co., Easton, PA 18042).

Wingo, P.A. et al., "Cancer Statistics, 1995," *CA Cancer Journal for Clinicians (A Journal of the American Cancer Society), 45(1)*:30 (1995).

Dodd, R.C. et al., "Vitamin D metabolites change the phenotype of monoblastic U937 cells," *Proc. Natl. Acad. Sci., USA. 80:*7538–7541 (Dec., 1983).

Gao, Y. et al., "The Effects of Chemotherapy Including Cisplatin on Vitamin D Metabolism," *Endocrine Journal, 40(6)*:737–742 (1993).

* cited by examiner

PREVENTION OF OVARIAN CANCER BY ADMINISTRATION OF PROGESTIN PRODUCTS

This application is a continuation-in-part of U.S. Ser. No. 08/713,834 filed Sep. 13, 1996.

FIELD OF THE INVENTION

The present invention relates generally to methods of preventing the development of ovarian cancer by administering progestin products, alone or in association with other agents which promote apoptosis.

BACKGROUND OF THE INVENTION

Ovarian cancer is the fourth leading cause of cancer deaths among women in the United States and causes more deaths than all other gynecologic malignancies combined. In the United States, a woman's lifetime risk of developing ovarian cancer is 1 in 70. In 1992, about 21,000 cases of ovarian cancer were reported, and about 13,000 women died from the disease. [Chapter 321, *Ovarian Cancer, Harrison's Principles of Internal Medicine*, 13th ed., Isselbacher et al., eds., McGraw-Hill, New York (1994), pages 1853–1858; *American Cancer Society Statistics, Cancer J. Clinicians*, 45:30 (1995). Epithelial ovarian cancer, the most common ovarian cancer, has a distinctive pattern of spread in which cancer cells migrate through the peritoneum to produce multiple metastatic nodules in the visceral and parietal peritoneum and the hemidiaphragms. In addition, metastasis occurs through the lymphatic and blood vessels to areas such as the liver, lung and brain, Early stage ovarian cancer is often asymptomatic and is detected coincidentally by palpating an ovarian mass on pelvic examination. In premenopausal patients, about 95% of these masses are benign. Even after menopause, 70% of masses are benign but detection of any enlargement requires exploratory surgery. In postmenopausal women with a pelvic mass, a markedly elevated serum CA-125 level of greater than 65 U/ml indicates malignancy with a 96% positive predictive value. [Chapter 321, *Ovarian Cancer, Harrison's Principles of Internal Medicine*, supra.]

Epithelial ovarian cancer is seldom encountered in women less than 35 years of age. Its incidence increases sharply with advancing age and peaks at ages 75 to 80, with the median age being 60 years. The single most important risk factor for this cancer is a strong family history of breast or ovarian cancer. In families in which ovarian, breast, endometrial or colon cancer can be tracked as an apparent autosomal dominant trait, the risk of this cancer can be as high as 50%. Having a single first-degree relative with ovarian cancer increases a woman's risk by at least three-fold, and having a personal history of breast or colorectal cancer increases the risk of subsequently developing ovarian cancer by two-fold. [Chapter 321, *Ovarian Cancer, Harrison's Principles of Internal Medicine*, supra.] In addition, those with identifiable genetic mutations in genes such as BRCA1 also have an increased risk. Baker et al., *Etiology, Biology, and Epidemiology of Ovarian Cancer, Seminars in Surgical Oncology* 10: 242–248, 1994; Amus et al., *Genetic Epidemiology of Epithelial Ovarian Cancer, Cancer* 71: 566–72, 1993; Whitmore, *Characteristics Relating To Ovarian Cancer Risk: Implications for Preventing and Detection, Gynecologie Oncology* 55, 515–19, 1994. Oncogenes associated with ovarian cancers include the HER-2/neu (c-erbB-2) gene, which is overexpressed in a third of ovarian cancers, the fins oncogene, and abnormalities in the p53 gene, which are seen in about half of ovarian cancers. A number of environmental factors have also been associated with a higher risk of epithelial ovarian cancer, including a high fat diet and intake of lactose in subjects with relatively low tissue levels of galactose-1-phosphate uridyl transferase.

In epidemiological studies, behavior associated with decreased ovulation, such as pregnancy, breastfeeding and use of estrogen-progestin combination oral contraceptive medications, decrease the risk of ovarian cancer; use of estrogen-progestin combination oral contraceptives for as long as 5 years can reduce the risk of ovarian cancer by 50%. Greene et al., *The Epidemiology of Ovarian Cancer, Seminars Oncology*, 11: 209–225, 1984; Whitmore et al., *Characteristics Relating To Ovarian Cancer Risk: Collaborative Analysis of 12 U.S. Case-Control Studies, American J. Epidemiology* 136: 1212–20, 1992. Conversely, early menarche, late menopause and nulliparity (no pregnancies) have been shown to increase the risk of ovarian cancer. The risk has been shown to positively correlate with the number of ovulatory cycles in a woman's lifetime. Wu et al., *Personal and Environmental Characteristics Related To Epithelial Ovarian Cancer, American J. Epidemiology*, Vol. 108(6) 1216–1227. The long-term use of ovulation-inducing ovarian hyperstimulants such as clomiphene has been shown to be associated with an increased risk of ovarian cancer in some women. Rossary et al., *Ovarian Tumors in a Cohort Of Infertile Women, New Eng. J. Med.*, 331: 771–6, 1994. Thus, some factors that favor prolonged and persistent ovulation have been thought to increase ovarian cancer risk, whereas some factors that suppress ovulation have been thought to decrease risk. [Chapter 321, *Ovarian Cancer, Harrison's Principles of Internal Medicine*, supra.] These data have led to the "incessant ovulation" hypothesis for the development of ovarian cancer. Casagrande et al., "Incessant Ovulation" and Ovarian Cancer, Lancet at 170–73 (Jul.28, 1979). This hypothesis is that repeated ovulation cycles, each of which involves the disruption and repair of the ovarian surface epithelium, may cause neoplastic transformation of the ovarian epithelium in susceptible individuals and that the risk of ovarian cancer is associated with the number of ovulation cycles in a woman's lifetime.

There is no established pharmaceutical approach to the prevention of ovarian cancer. For all women, especially those at high risk of developing this disease, the only option available at this time is surgical removal of the ovaries, with all of the attendant risks and subsequent adverse health consequences due to resulting estrogen deficiency.

Although epidemiological evidence suggests that the use of combination oral contraceptives, which contain both an estrogen and a progestin, is associated with a subsequent reduced risk of developing epithelial ovarian cancer, the mechanism for this protective effect is unknown, and oral contraceptive preparations are not currently approved for this purpose. The reduction in risk of ovarian cancer in women who have used estrogen-progestin combination oral contraceptives for at least three years is approximately 40 percent. Moreover, this protective effect increases with the duration of use and persists for up to two decades after discontinuation of use. Rosenberg et al., *A Case Control Study of Oral Contraceptive Use and Invasive Epithelial Ovarian Cancer, The WHO Collaborative Study of Neoplasia and Steroid Contraceptives; Epithelial Ovarian Cancer and Combined Oral Contraceptives, Int'l J. Epidemiology* 18: 538–45, 1989; Lee et al., *The Reduction in Risk of Ovarian Cancer Associated with Oral Contraceptive Use, New Engl. J. Med.* 316: 650–51, 1987; Thomas P. Gross, James J. Schlesselman, *The Estimated Effect of Oral Contraceptive Use on the Cumulative Risk of Epithelial Ovarian Cancer*, Obstetrics Gynecology 83: 419–24, 1994; Franceschi et al., *Pooled Analysis of 3 European Case-Control Studies of Epithelial Ovarian Cancer: III. Oral Contraceptive Use*, Int'l J. Cancer 49: 61–65, 1991.

It is commonly believed that the protective effect of oral contraceptives is related to the ability of these drugs to inhibit ovulation. Estrogen-progestin combination oral contraceptives act primarily by suppressing the pituitary gland's production of gonadotropins, thereby inhibiting the hormonal stimulus for ovulation. These combination drugs also have direct inhibitory effects on the reproductive tract, including inducing changes in the cervical mucus that decrease the ability of sperm to enter the uterus, as well as changes in the endometrium that reduce the likelihood of implantation, and reducing fallopian tube motility and uterine secretions.

The epidemiological studies showing the protective effect of combination oral contraceptives evaluated older combination preparations which typically contained higher doses of drug than most contraceptive regimens used today. Common older regimens contained 50 micrograms or more of ethinyl estradiol (an estrogen) or 100 micrograms or more of mestranol (an estrogen) and greater than 1 mg of norethindrone, norethindrone acetate or norethynodrel (a progestin). Table 1 infra lists the progestin and estrogen content of some older regimens. All of the currently used low-dose combination oral contraceptives contain lower doses of both progestin and estrogen, as well as a lower ratio of progestin to estrogen. Consequently, it has not been definitively established that the newer low-dose combination oral contraceptives are associated with the same protective effect as the older high-dose combination contraceptives. Rosenblatt et al., *High Dose and Low Dose Combined Oral Contraceptives: Protective Against Epithelial Ovarian Cancer and The Length of the Protective Effect*, Eur. J. Cancer, 28: 1870–76, 1992.

Despite the overall safety of combination oral contraceptives, their use is not recommended for women smokers older than age 35, for women of all ages who are at increased risk for myocardial infarction, for women with liver disease, and for women older than age 40. Serious and potentially fatal side effects include deep vein thrombosis, pulmonary emboli, myocardial infarction, thromboembolic stroke, hemorrhagic stroke, and high blood pressure. In the 35–39 year old age group, the use of oral contraceptives among women smokers doubles their risk of death. After age 40, the mortality rate even in non-smoker women using oral contraceptives (32.0 per 100,000) is greater than women using no contraception (28.2 per 100,000), while the mortality rate for smoker women is quadrupled (117.6 vs. 28.2 per 100,000). [Chapter 340, *Disorders of the Ovary and Female Reproductive Tract, Harrison's Principles of Internal Medicine*, supra, pages 2017–2036.]

Progestin-only contraceptives do not reliably inhibit ovulation, but are nevertheless contraceptively effective, presumably due to direct effects on the reproductive tract. The actual contraceptive mechanism of action is unclear. Prior epidemiological studies have exhibited no consistent pattern of either increasing or decreasing risk of ovarian cancer according to duration of use. *The WHO Collaborative Study of Neoplasia and Steroid Contraceptives Depot-Medroxyprogesterone Acetate(DMPA) and Risk of Epithelial Ovarian Cancer*, Int'l J. Cancer. 49:191–195 (1991); Liam et al., *Risk of Breast, Uterine, Corpus, and Ovarian Cancer in Women Receiving Medroxyprogesterone Injections*, J. Am. Med. Ass'n 249:2909–2912 (1983). Thus, unlike the data available for progestin-estrogen combination contraceptives, the prior art relating to progestin-only contraceptives does not suggest that the use of a progestin reduces the risk of epithelial ovarian cancer.

Estrogen, alone or with low doses of progestin, is also used as hormonal replacement therapy in menopausal women. For long term use, Premarin® (conjugated equine estrogen) is generally given at a dose of 0.625 mg orally daily (equivalent to 10 to 20 µg ethinyl estradiol orally per day) or an equivalent dose transdermally. Other regimens add cyclic progestins or continuous low-dose progestins, typically 2.5 to 10 mg per day of Provera® (medroxyprogesterone acetate). One epidemiologic study has suggested that hormone replacement therapy with estrogen alone may be associated with an increased risk of developing ovarian cancer. Rodriguez et al., *Estrogen Replacement Therapy and Fatal Ovarian Cancer*, Am. J. Epidemiology, 141:828–835 (1995).

SUMMARY OF THE INVENTION

The present invention provides a method for preventing the development of epithelial ovarian cancer by administering progestin products, either alone or in combination with other agents, such as estrogen products. A method is provided of preventing ovarian cancer comprising administering to a female subject an amount of progestin product effective to increase apoptosis in ovarian epithelial cells of the female subject.

It is further the object of this invention to expand the clinical usage of progestin drugs beyond the current use of these drugs as oral contraceptive agents in young women or as part of estrogen-progestin hormone replacement regimens in postmenopausal women. One aspect of the invention provides a method for preventing the development of ovarian cancer comprising administering to a female subject a composition consisting essentially of a progestin product (i.e., a progestin product alone without an estrogen product).

The invention also provides a method for preventing the development of ovarian cancer comprising administering a progestin product to a female subject according to a regimen that is not effective for contraception. This can be accomplished in a number of ways, including altering the dosage of progestin product, the type of progestin product, the ratio of progestin product to estrogen product, or the timing of administration.

With regard to infertile female subjects, the present invention further provides a method for preventing the development of ovarian cancer comprising administering a progestin product according to a regimen that is different from that currently used for hormone replacement therapy. Again, this can be accomplished in a number of ways, including altering the dosage, timing, ratio of progestin product to estrogen product, or the type of progestin product.

It is contemplated that the progestin product may be concurrently administered in combination with additional agent(s), such as an estrogen product, a second progestin product, an androgenic agent, an androgen agonist, a progestin agonist, an estrogen antagonist, or another hormone product, or with other agents that induce apoptosis of ovarian epithelial cells including those selected from the group consisting of the retinoids, dietary flavanoids, anti-inflammatory drugs, monoterpenes, S-adenosyl-L-methionine, selenium and vitamin D compounds. Such additional agent(s) may be selected to improve the activity of the progestin agent for preventing ovarian cancer or to reduce any side effects of the progestin agent. Preferably if estrogen is used as the second agent, it is used in doses lower than those currently used in combination oral contraceptive regimens or in doses selected to provide a progestin/estrogen product ratio that is higher than the ratio currently used in combination oral contraceptives.

The present invention is based on the discovery that administration of progestin alone induced an accelerated rate of apoptosis in vivo in ovarian epithelial cells of monkeys. Apoptosis is one of the most important mechanisms used for the elimination of cells that have sustained DNA damage and which are thus prone to transformation into malignant neoplasms. This novel explanation for the association between estrogen-progestin combination oral contraceptive use and a reduced risk of ovarian cancer is a complete departure from the widely accepted theory that suppression of "incessant ovulation" is responsible for this reduced risk. This finding thus relates to the discovery that progestin alone or estrogen-progestin combinations may be administered in ways that do not effectively inhibit ovulation or otherwise inhibit contraception, yet which still prevent ovarian cancer.

The invention further relates to the discovery that progestin alone induced a greater rate of apoptosis than a combination of estrogen and progestin, which in turn induced a greater rate of apoptosis than estrogen alone. The invention thus contemplates that administration of progestin alone be effective for preventing the development of ovarian cancer, contrary to the suggestions of the prior art that progestin has no effect on risk of ovarian cancer. In addition to providing the use of high dosages of progestin products, high potency progestin products and/or high ratios of progestin products to estrogens in promoting apoptosis of ovarian epithelial cells to prevent ovarian cancer, the invention provides the use of progestin products in combination with other apoptosis promoting agents selected from the group consisting of the retinoids, dietary flavanoids, anti-inflammatory drugs, monoterpenes, S-adenosyl-L-methionine, selenium and vitamin D compounds to promote apoptosis in ovarian epithelial cells.

DETAILED DESCRIPTION OF THE INVENTION

The present invention generally relates to methods for preventing the development of epithelial ovarian cancer by administering a progestin product, either alone or in combination with other agents, such as an estrogen product. The invention provides a method of preventing ovarian cancer comprising administering to a female subject an amount of progestin product effective to increase apoptosis in ovarian epithelial cells of the female subject. The invention also provides a method of increasing apoptosis in ovarian epithelial cells of a female subject comprising administering to a female subject an amount of progestin product effective to increase apoptosis in ovarian epithelial cells of the female subject. In particular, the methods of the present invention will be particularly advantageous when applied to females at high risk of developing ovarian cancer. As a further aspect of the invention it is contemplated that the methods and regimens of doses of the present invention which use high dosages of progestins, high potency progestins and/or high ratios of progestins to estrogens may be effective in preventing the occurrence of endometrial cancer.

In a second aspect of the invention, a method is provided for preventing the development of ovarian cancer comprising administering to a female subject a composition consisting essentially of a progestin product (i.e., a progestin product alone without an estrogen product). The female subject may be a fertile female or an infertile female, including perimenopausal and postmenopausal women. The most preferred product for administration would be an agent that provides the greatest rate of apoptosis of ovarian epithelial cells with the least side effects. Use of a progestin product for longer durations, or at higher doses, at appropriate intervals, and/or use of an agent that maximizes apoptosis, without creating unacceptable side effects, in fertile or infertile women may reduce the risk of ovarian cancer further than that previously achieved by combination oral contraceptive use, potentially by as much as 60% to 80%.

The invention further contemplates expanding the clinical usage of progestin drugs beyond the current use of these drugs as oral contraceptive agents in young women or as part of estrogen-progestin hormone replacement regimens in postmenopausal women. Specifically, a third aspect of the present invention provides a method for preventing the development of ovarian cancer comprising administering a progestin product to a fertile female subject according to a regimen that is not effective for contraception. This can be accomplished in a number of ways, including altering the dosage of progestin product, the type of progestin product, the ratio of progestin product to estrogen product, or the timing of administration. Also specifically contemplated is administration of a progestin product in doses higher than those currently used for contraception.

Oral contraceptive administration regimens are selected to simulate the normal menstrual cycle, which averages 28 days in women of reproductive age. The menstrual cycle begins at the onset of a menstrual bleeding episode and lasts until the onset of the next. Thus, day 1 of a cycle would be the first day of menstruation, and day 28 would be the day before the onset of the next menstrual bleeding episode. Oral contraceptives are typically taken daily, at the same time each day, for 21 days, followed by a placebo for the next 7 days. The female generally experiences a menstrual bleeding episode during the seven-day placebo period. Thus, a woman first starting on oral contraceptives is generally instructed to begin taking them at some time between day 1 and 7.

The oral contraceptives must be taken according to the daily regimen for a full menstrual cycle before they are effective for contraception. A woman beginning an oral contraceptive regimen is not effectively protected against conception if the oral contraceptives are taken for less than the full menstrual cycle, if they are not taken daily, and if they are not taken for 21 consecutive days. A minimum blood level of the exogenously administered estrogen or progestin hormones must be maintained daily in order to suppress ovulation. If the blood level drops too low, ovulation may occur and the other inhibitory mechanisms on the reproductive tract may fail to prevent conception.

Thus, according to this third aspect of present invention, a regimen of progestin product administration that is not effective for contraception would include, for example, administering or delivering (regardless of whether the route of administration is oral or via injection or implant) progestin products in doses lower than those effective for contraceptive use and/or lower than those previously used in contraceptives; administering progestin products with estrogen products at a progestin/estrogen ratio that is higher than that previously used in contraceptives; administering the drug for less than one menstrual cycle; administering the drug for nonconsecutive menstrual cycles, e.g., every other cycle; administering the drug for one or more menstrual cycles for fewer than 21 consecutive days in each cycle; delivering the drug (regardless of whether the route of administration is oral or via injection or implant) with a less than daily frequency; or administering the drug for one or more menstrual cycles according to a regimen that fails to maintain a contraceptive blood level of the drug or its active metabolite for 21 consecutive days in each cycle. A regimen of progestin product administration that is different from that currently used for contraception would also include administering the progestin product at a daily dose higher than that currently used for contraception.

Exemplary regimens according to this third aspect of the invention include administering progestin product at a dose higher than 5 mg daily and preferably 10 mg daily of a norethindrone equivalent dose. Another exemplary regimen includes administering progestin product at a dose less than a dose equivalent to 1 mg daily of norethindrone, more preferably less than 0.2 mg daily, or less than 0.05 mg daily, and possibly as low as 0.025 mg daily of a norethindrone equivalent dose. A further exemplary regimen includes administering a progestin product with an estrogen product at a ratio of greater than 100:1 by weight in norethindrone/ethinyl estradiol equivalent doses with a ratio greater than 239:1 by weight being preferred. Additional exemplary regimens include administering any dose of progestin product with a less than daily frequency; or administering any dose of progestin product for a brief time, e.g., one week only, during the menstrual cycle. It is contemplated that the most desirable mode of administration may be administering the progestin product for a brief period sufficient to produce apoptotic turnover of damaged ovarian cells, followed by repeated dosing periods at intervals, for example monthly, two to six times per year or 1, 3, 5 or 10 years, selected to provide apoptotic turnover adequate to prevent malignant transformations. The most preferable progestin product for administration would be a product that maximizes the apoptotic turnover of ovarian epithelial cells and minimizes any side effects.

The fourth aspect of the present invention provides a method for preventing the development of ovarian cancer in infertile female subjects, comprising administering a progestin product according to a regimen that is different from that currently used for hormone replacement therapy. Again, this can be accomplished in a number of ways, including altering the dosage, timing, ratio of progestin product to estrogen product, or the type of progestin product. Other contemplated regimens would include, for example, administering or delivering progestin product in doses lower or higher than those previously used in hormone replacement therapy; or administering progestin product with estrogen product at a progestin/estrogen ratio that is higher than that previously used in hormone replacement therapy.

Estrogen is the primary agent in hormone replacement therapy. Postmenopausal women are generally given estrogen alone, or with low doses of progestins. The hormones may be administered continuously or cyclically. Continuous administration is typically 0.625 mg Premarin® (a conjugated equine estrogen) daily or its equivalent, with 2.5 mg Provera® (medroxyprogesterone acetate) daily. Cyclical administration is typically 25 consecutive days of 0.625 mg Premarin® daily, with 10 mg Provera® daily on days 16 through 25, followed by 5 days of no hormone treatment (during which time these women will menstruate).

Exemplary regimens according to the fourth aspect of the present invention include doses of progestin product less than a dose equivalent to 2.5 mg of medroxyprogesterone acetate daily (equivalent to about 1.25 mg of norethindrone), or less than 0.5 mg daily of a norethindrone equivalent dose. Another exemplary regimen includes a dose of progestin product greater than a dose equivalent to 10 mg of medroxyprogesterone acetate daily (equivalent to about 5 mg of norethindrone) for 10 days every month. Alternatively, a regimen useful according to the invention is that by which is administered a cumulative monthly dosage greater than the equivalent of 50 mg or more preferably 100 mg of norethindrone. Thus, the invention provides progestin product dosages which are greater than those currently administered on a daily and/or monthly basis.

A further exemplary regimen includes doses of progestin product with estrogen product at a ratio of greater than 1:1 by weight in norethindrone/ethinyl estradiol equivalent doses, or a ratio of greater than 50:1 or 100:1. It is also contemplated that the most desirable mode of administration may be administering the progestin product for a brief period sufficient to produce apoptotic turnover followed by repeated dosing periods at selected intervals adequate to prevent malignant transformations. A presently preferred progestin product is levonorgestrel or other 19-nortestosterone derivatives. The most preferable progestin product for administration would be a product that maximizes the apoptotic turnover of ovarian epithelial cells and minimizes any side effects.

The present invention yet further provides a novel use of progestin product in preparation of a non-contraceptive medicament for prevention of ovarian cancer in female subjects, as well as a novel use of progestin product in preparation of a medicament for prevention of ovarian cancer in infertile female subjects.

Accordingly, the invention provides therapeutic compositions and methods for promotion of apoptosis of ovarian epithelial tissue and prevention of ovarian cancer by their administration which compositions comprise a progestin product and an apoptosis promoting agent selected from the group consisting of the retinoids, dietary flavanoids, anti-inflammatory drugs, monoterpenes, S-adenosyl-L-methionine, selenium and vitamin D compounds together in amounts effective to increase apoptosis in ovarian epithelial cells of a female subject. Such compositions may be administered by a variety of means including orally and by injection but may also be administered in the form of sustained release products by means selected from the group consisting of implants and transdermal patches.

According to each of the preceding and following aspects of the invention comprising multiphase regimens for administration of progestin products the additional apoptosis promoting agent may be administered simultaneously with the progestin product or alternatively may be administered during a phase when the progestin product is not administered.

Further exemplary methods of preventing ovarian cancer according to the invention (e.g., methods beyond the use of estrogen and progestin products as oral contraceptive agents or as hormone replacement regimens in postmenopausal women) and corresponding exemplary regimens of doses are provided as follows.

One exemplary method (e.g., in premenopausal women) comprises administering to a female subject a multiphase regimen comprising a first phase in which an estrogen product is administered in combination with a progestin product; a second phase in which an estrogen product is administered in combination with a progestin product; and a third phase in which a progestin product is not administered; and wherein said first phase is about 14 days (2 weeks) or longer, or alternatively about 21 days or longer, or alternatively about 28 days or longer (e.g., greater than about 30, or 60, or 90, or 120 or 180 or 360 days) and wherein the progestin product administered in said second phase is at a dose effective to promote (or increase) apoptosis and is characterized by at least twice, three-fold, 5-fold, 7-fold, 10-fold or 15-fold the effective dosage of the progestin product administered in said first phase. In premenopausal women, appropriate dosages in all phases may be selected to provide contraceptive effects as well, and dosages during the third phase may be selected so as to result in menses.

Another exemplary method of preventing ovarian cancer comprises administering to a female subject a multiphase regimen comprising a first phase in which an estrogen product is administered; a second phase in which an estrogen product is administered in combination with a progestin product; and optionally a third phase in which a progestin product is not administered; and wherein said first phase is about 14 days (2 weeks) or longer, or alternatively about 21 days or longer, or alternatively about 28 days or longer (e.g., greater than about 30, or 60, or 90, or 120 or 180 or 360 days) and wherein the progestin product administered in said second phase is characterized by a dosage less than sufficient to prevent ovulation yet is a dose effective to promote apoptosis.

A further exemplary method of preventing ovarian cancer comprises administering to a female subject a multiphase regimen comprising a first phase in which an estrogen product is administered; a second phase in which an estrogen product is administered in combination with a progestin product; and optionally a third phase in which a progestin product is not administered; and wherein said first phase is about 14 days (2 weeks) or longer, or alternatively about 21 days or longer, or alternatively about 28 days or longer (e.g., greater than about 30, or 60, or 90, or 120 or 180 or 360 days) and wherein the estrogen product administered in said first or second phase is characterized by a dosage less than sufficient to prevent ovulation and wherein the progestin product administered in said second phase is at a dose effective to promote apoptosis.

Such methods characterized by administration of estrogen or progestin products at doses less than sufficient to prevent ovulation are particularly suitable for postmenopausal women.

According to an alternative aspect of the invention a method is provided of preventing ovarian cancer comprising administering to a female subject a multiphase regimen comprising a first phase in which an estrogen product is administered in combination with a progestin product; a second phase in which an estrogen product is administered in combination with a progestin product wherein the estrogen product is administered at a lower effective dosage than in said first phase; and a third phase in which an estrogen product is administered with a progestin product wherein the progestin product is administered at a higher effective dosage than in said first and second phases and promotes apoptosis. Preferably the multiphase regimen has no breaks in hormone administration which would result in breakthrough bleeding, and would thus be particularly suitable for postmenopausal women.

The invention further provides a regimen of doses for prevention of ovarian cancer by promoting apoptosis in ovarian epithelial cells comprising a multiphase sequence of pharmaceutical dosages comprising a first series of dosages comprising an estrogen product and a progestin product; and a second series of dosages comprising an estrogen product and a progestin product; and wherein the number of dosages in the first series is sufficient for daily administration for a period of about 14 days (2 weeks) or longer, or alternatively about 21 days or longer, or alternatively about 28 days or longer (e.g., greater than about 30, or 60, or 90, or 120 or 180 or 360 days) and wherein the dosage of progestin product in said second series is effective to promote apoptosis and is characterized by at least twice, three-fold, 5-fold, 7-fold, 10-fold or 15-fold the effective dosage of the progestin product in said first series. According to a preferred aspect this regimen further comprises a third series of dosages which are a placebo (to provide menses).

Additional regimens of dosages for prevention of ovarian cancer are those regimens for prevention of ovarian cancer comprising a multiphase sequence of pharmaceutical dosages comprising a first series of dosages comprising an estrogen product; and a second series of dosages comprising an estrogen product and a progestin product; and wherein the first series of dosages is sufficient for daily administration for a period of about 14 days (2 weeks) or longer, or alternatively about 21 days or longer, or alternatively about 28 days or longer (e.g., greater than about 30, or 60, or 90, or 120 or 180 or 360 days) and wherein the dosage of the progestin product in said second series is characterized by a dosage less than sufficient to prevent ovulation yet effective to promote apoptosis. Alternatively, the dosage of the estrogen product in said second series is characterized by a dosage less than sufficient to prevent ovulation and the dosage of the progestin product in said second series is effective to promote apoptosis.

The invention further provides a regimen of dosages for prevention of ovarian cancer comprising a multiphase sequence of pharmaceutical dosages comprising a first series of dosages comprising an estrogen product and a progestin product; a second series of dosages comprising an estrogen product and a progestin product wherein said estrogen product is administered at a lower effective dosage than in said first series; and a third series of dosages comprising a progestin product and an estrogen product wherein said progestin product is administered at a higher effective dosage than in said first series and promotes apoptosis. According to one preferred aspect of the invention, an additional apoptosis promoting agent may be combined with the progestin product in the third series. Alternatively, an additional apoptosis promoting agent may be administered during the first series.

According to one aspect of the invention, a regimen is provided which is contraceptive but which provides a particularly high dosage of a progestin product on a less frequent than a monthly basis designed to maximize the apoptotic effect of the progestin administration. Such regimens can include 60-day, 90-day, 180-day, 360-day and other regimens representing a duration of more than a single menstrual cycle.

Examples of 90 day regimens according to this aspect of the invention include those comprising administration for days 1–70 of a combination estrogen/progestin product such as 0.010 mg, 0.020 or 0.030 ethinyl estradiol +0.05 mg levonorgestrel or 0.010 mg, 0.020 mg or 0.03 mg ethinyl estradiol +0.075 mg levonorgestrel. During days 71–85 a different combination estrogen/progestin product is administered such as 0.030 mg ethinyl estradiol +0.15 mg or 0.25 mg or 0.5 mg levonorgestrel. This is then followed on days 86–90 with no drug administration or administration of a placebo. One effect of such a regimen is that menses would occur only once every three months corresponding to the period of administration of placebo. Such regimens could be altered with respect to dosages and timing and equivalent regimens could be prepared using combinations of other progestin and estrogen products according to the skill in the art.

Examples of 180 day regimens according to this aspect of the invention include those comprising administration for days 1–160 of a combination estrogen/progestin product such as 0.010 mg ethinyl estradiol +0.05 mg levonorgestrel or 0.020 mg ethinyl estradiol +0.05 mg levonorgestrel or 0.010 mg ethinyl estradiol+0.075 mg levonorgestrel or 0.020 mg ethinyl estradiol +0.075 levonorgestrel. During days 161–175 a different combination estrogen/progestin product is administered such as 0.030 mg ethinyl estradiol +0.15 mg, or 0.25 mg or 0.5 mg levonorgestrel. This is then followed on days 176–180 with no drug administration or administration of a placebo. Menses would then generally result only once every six months.

Other combination progestin/estrogen regimens are contemplated by the invention characterized by higher progestin to estrogen ratios.

The invention also provides preferred regimens for prevention of ovarian epithelial cancer in postmenopausal women who do not require a regime which is contraceptive but may be desirous of hormone replacement therapy. Thus, there is desired sufficient estrogen product to provide both bone protection and cardiac protection effects. Any suitable estrogen product can be used which provides these therapeutic effects. Thus, it is known that estrogen products having different affinities and activities with different estrogen receptors (ERα and Erβ) and different subspecies of those receptors can be selected to provide the desired estrogenic effects.

According to one aspect of the invention, a regimen of dosages protective of ovarian epithelial cancer is provided for postmenopausal women with no uterus. Such a regimen provides essentially cyclic doses of high levels of progestin with or without estrogen. Suitable periodic regimens according to this aspect of the invention include a 30 day regimen comprising administration of an estrogen product alone such as at levels of 0.325 or 0.625 mg of conjugated estrogen for days 1–14 followed by a combination estrogen product with 0.15 mg or 0.25 mg or more levonorgestrel for days 15–25 followed by a placebo for days 26–30. Similar 60-day, 90-day, 180-day, 360-day and other regimens lasting multiples of 30 days and the like could be administered wherein, for example, an estrogen product is administered alone during days 1–40, 1–70, 1–160 or 1–340 respectively followed by administration of the combination estrogen/progestin product during days 41–55, 71–85, 161–175 or 341–355 and then followed by five days of a placebo (or no drug administration), respectively. Regimens of dosages (kits) providing such regimens can be supplied or kits comprising the progestin product component of such regimens can be provided to supplement an estrogen-only hormone replacement regimen in order to provide an ovarian cancer protective effect.

According to another aspect of the invention, a regimen for prevention of ovarian cancer in postmenopausal women is provided which is similar to that used in premenopausal women but would use the lowest dosages of estrogen and progestin products possible in combination with cyclic high dosages of progestin to achieve protection. According to one such regimen a dosage of estrogen comparable to 0.325mg or 0.625 conjugated estrogen, i.e. 0.010 or 0.015 mg ethinyl estradiol, plus 0.05 levonorgestrel is administered daily for days 1–70 followed by administration on days 71–85 of the same dosage of an estrogen product plus 0.15 or 0.25 mg or more of levonorgestrel. A placebo (or no drug) is administered on days 86–90.

According to another regimen of the invention a progestin product is administered by sustained release such as by means of an implant which releases about 0.05 mg of levonorgestrel or its equivalent per day and is supplemented by administration of other apoptosis promoting agents such as a member selected from the group consisting of the retinoids, dietary flavanoids, anti-inflammatory drugs, monoterpenes, S-adenosyl-L-methionine, and Vitamin D products. The invention further provides regimens wherein the progestin product is administered at very high levels over short periods of time or where low levels of progestin products are administered followed by high levels for short durations. According to one example, progestin products are administered on a daily basis at levels of 0.05 mg levonorgestrel or less followed by administration of high levels of 0.15, 0.25, or 0.5 mg or more levonorgestrel for periods 10 of 7to14days.

A further ovarian cancer prevention regimen according to the invention comprises hormone administration to postmenopausal women with uterus which is continuous with no breaks and which therefore achieves its effects while preventing breakthrough bleeding. A 60-day regimen according to this aspect of the invention comprises administration of 0.015 mg ethinyl estradiol plus 0.05 mg levonorgestrel for days 1–14 followed by administration of 0.010 mg ethinyl estradiol plus 0.05 mg levonorgestrel for days 15–40 followed by administration of 0.010 mg ethinyl estradiol plus 0.15 mg or 0.25 mg or more levonorgestrel for days 41–60.

All doses given herein are appropriate for a female subject of about 60 kg weight; the dosages naturally will vary more or less depending on the weight of the subject. The doses may be increased or decreased, and the duration of treatment may be shortened or lengthened as determined by the treating physician. The frequency of dosing will depend on the pharmacokinetic parameters of the agents and the route of administration. The optimal pharmaceutical formulation will be determined by one skilled in the art depending upon the route of administration and desired dosage. See for example, Remington's Pharmaceutical Sciences, 18th Ed. (1990, Mack Publishing Co., Easton, Pa. 18042) pages 1435–1712, the disclosure of which is hereby incorporated by reference. Such formulations may influence the physical state, stability, rate of in vivo release, and rate of in vivo clearance of the administered agents.

Those of ordinary skill in the art will readily optimize effective dosages and concurrent administration regimens as determined by good medical practice and the clinical condition of the individual patient. Regardless of the manner of administration, the specific dose may be calculated according to body weight, body surface area or organ size. Further refinement of the calculations necessary to determine the appropriate dosage for treatment involving each of the above mentioned formulations is routinely made by those of ordinary skill in the art and is within the ambit of tasks routinely performed by them without undue experimentation, especially in light of the dosage information and assays disclosed herein. Appropriate dosages may be ascertained through use of established assays for determining dosages in conjunction with appropriate dose-response data. The final dosage regimen will be determined by the attending physician, considering various factors which modify the action of drugs, e.g. the drug's specific activity, the severity of the damage and the responsiveness of the patient, the age, condition, body weight, sex and diet of the patient, the severity of any infection, time of administration and other clinical factors. As studies are conducted, further information will emerge regarding the appropriate dosage levels for the treatment of various diseases and conditions.

It is contemplated that the routes of delivery of progestin products (either alone or in combination with other pharmaceuticals) could include oral, sublingual, injectable (including short-acting, depot, implant and pellet forms injected subcutaneously or intramuscularly), vaginal creams, suppositories, pessaries, rings, rectal suppositories, intrauterine devices, and transdermal forms such as patches and creams.

The present invention is related to the discovery that administration of progestin alone induced an accelerated rate of apoptosis in vivo in ovarian epithelial cells of monkeys. Apoptosis is a process whereby a genetic program within the cell is activated to trigger a specific series of events within the cell eventually leading to the death and efficient disposal of the cell. Richard Lockshin, Zahra Zakeri, *The Biology of Cell Death and Its Relationship to Aging in Cellular Aging and Cell Death,* pp. 167–180, 1996. Wiley-Liss Inc., Editors: N. J. Holbrook, G. Martin, R. Lockshin. C. Miligan, L. Schwartz, *Programmed Cell Death During Development of Animals in Cellular Aging and Cell Death,* pp. 181–208, 1996. Wiley-Liss Inc. P53-*Dependent Apoptosis in Tumor Progression and in Cancer Therapy,* Scott W. Lowe, H. Earl Ruley in *Cellular Aging and Cell Death, pp.* 209–234, 1996. Wiley-Liss, Inc.

For cells that have sustained DNA damage, apoptosis is one of the most important mechanisms used for the elimination of these cells, the preservation of which could otherwise lead to the development of malignant neoplasms. Canman et al., *DNA Damage Responses: P-53 Induction, Cell Cycle Pertubations, and Apoptosis, Cold Spring Harbor Symp. Quant. Biol.,* 59:277–286 (1994). Thus, the apoptosis pathway is a virtually universal safeguard to prevent the persistence and proliferation of damaged cells that can be lethal to the organism. For normal tissues, the processes of cell proliferation and cell death are usually in a steady-state balance, and the apoptosis mechanism not only serves to prevent overgrowth of tissue, but also to eliminate those cells that are aberrant and therefore prone to resist normal growth regulatory controls.

An accelerated rate of apoptosis would facilitate the destruction and thereby removal of ovarian surface epithelial cells which have defective DNA and which have the potential to transform into malignant neoplasms. Given the importance of the apoptotic pathway for removal of abnormal cells from tissues, and thus the protection of normal tissues from neoplastic transformation, it is likely that the induction of apoptosis by progestins is one of the major (if not the major) mechanism underlying the effect of combination oral contraceptives in reducing the risk of ovarian cancer.

This novel explanation for the association between estrogen-progestin combination oral contraceptive use and a reduced risk of ovarian cancer is a complete departure from the widely accepted theory that suppression of "incessant ovulation" is responsible for this reduced risk. This finding thus leads to the discovery that progestin alone or estrogen-progestin combinations may be administered in ways that do not effectively inhibit ovulation or otherwise inhibit contraception, yet which still prevent ovarian cancer. Since the protective mechanism for progestin containing compounds is related to a direct biological effect on the ovarian epithelium, it is likely that the use of progestin drugs in postmenopausal women who are not ovulating will also be protective against the development of epithelial ovarian carcinoma.

The invention is further based on the discovery that use of progestin alone induces a more accelerated rate of apoptosis in vivo in ovarian epithelial cells of monkeys compared to the combination of estrogen and progestin, which in turn induced a greater rate of apoptosis than estrogen alone. The implications of this discovery are that the progestin component of the oral contraceptive is responsible for this effect, and that administration of progestin alone may be effective for preventing the development of ovarian cancer, contrary to established reports that it has no effect on risk of ovarian cancer. Since the human-equivalent dose of the progestin only dose given the monkeys is insufficient to reliably block ovulation in women, yet showed the greatest degree of apoptosis (and thus protection), this indicates that ovulatory blockade per se is not essential for the protective effect, and that progestin product only (or with estrogen product) in doses less than sufficient to prevent ovulation is effective in preventing ovarian cancer.

The term "progestin product" or "progestogenic agent" as used herein includes any drug which binds to the progestin receptor and induces a progestational effect. This definition thus includes all of the known progestins, derivatives of progesterone or testosterone that have progestin activity, progestin agonists, and any other agent that increases the rate of apoptosis in ovarian epithelial cells. It is contemplated that not only presently available progestins but also progestins introduced in the future will be useful according to the present invention. The known synthetic progestins are mainly derivatives of 17-alpha-hydroxy-progesterone or 19-nortestosterone. These progestins can be classified into three groups: the pregnane, estrane, and gonane derivatives. The pregnane progestins, derived from 17 alphahydroxy-progesterone, include, for example, medroxyprogesterone acetate, chlormadinone acetate, megestrol acetate, and cyproterone acetate. All of these are roughly 20% to 50% of the potency of norethindrone. The estranes, derived from 19-nortestosterone include norethindrone, norethynodrel, lynestrenol, norethindrone acetate, ethynodiol acetate, and norethindrone enanthate. All of these are metabolized to norethindrone and are roughly equivalent to the same dosage of norethindrone. The gonanes are derived from the basic estrane structure, with the addition of an ethyl group of position 13 of the molecule. This additional ethyl group confers augmented progestogenic activity, and also significant androgenic effects. Drugs in this group include, for example, norgestrel (-d and -1), norgestimate, desogestrel, and gestodene. All of these are roughly equivalent to four times the dose of norethindrone. The oral preparations currently on the market are: norgestrel 0.075 mg, medroxyprogesterone acetate 2.5 mg, 5.0 mg, and 10.0 mg, norethindrone 0.35 mg and 1.0 mg, and norethindrone acetate 0.50 mg.

Progestogenic agents have a variety of biological effects including antifertility, inhibition of midcycle luteinizing hormone surge, inhibition of ovulation, inhibition of corpus lutetium function and development, and production of a secretory endometrium. In addition, the progestins have important effects on carbohydrate metabolism, lipid and lipoprotein metabolism and have cardiovascular effects.

Progestogenic potency can be measured by other biological outcomes, including the ability of these agents to bind to the progesterone receptor. The progestogenic activity of the various progestin derivatives can vary. In a review of the literature, Dorflinger has noted that the progestogenic potency of all these estrane drugs is equivalent, and exhibit only 5–10 percent of the progestogenic activity of levonorgestrel.

In addition to their progestogenic effects, the synthetic progestins have the ability to bind to both estrogen and androgen receptors, to a varying degree. These drugs can therefore have estrogenic, androgenic, antiestrogenic or antiandrogenic effects. For example, the estrane progestins are weak estrogen agonists, and therefor have slight estrogen activity. In contrast, the gonane levonorgestrel has no estrogenic activity, but does have androgenic activity. The 19-nortestosterone derivatives have androgenic activity mediated by variable binding to the androgen receptor.

Given the diverse binding patterns of the different synthetic progestins to various receptors (progestin, androgen and estrogen receptors), the estrogenic, progestogenic and androgenic activity can vary among the different synthetic progestin formulations, thus leading to varying degrees of progestational activity and androgenic side effects. For example, the progestational binding activity of norethindrone is less than 20% that of levonorgestrel and less than 10% that of 3-ketodesogestrel, the active metabolite of the progestin desogestrel, while the binding affinity of norethindrone to the androgen receptor is similar to that of 3-ketodesogestrel, and yet both compounds have less than 50% of the nuclear cell androgenic activity of levonorgestrel.

It is contemplated that the progestins with more androgenic activity and less estrogenic activity, such as levonorgestrel, may be preferred as more potent for preventing the development of ovarian cancer. Such agents would include the 19-nortestosterone derivatives, such as norethindrone, norethynodrel, lynestrenol, norethindrone acetate, ethynodiol acetate, and norethindrone enanthate.

The term "estrogen product" as used herein includes ethinyl estradiol, mestranol (a 50 mg dosage of which is equivalent to 35 mg of ethinyl estradiol), conjugated equine estrogen, estrone, estradiol, esterified estrogens, estropipate, and other estrogen equivalents and estrogen agonists.

"Concurrent administration" or "co-administration" as used herein includes administration of the agents together, or before or after each other. The agents may be administered by different routes. For example, one agent may be administered intravenously while the second agent is administered intramuscularly, intravenously or orally. They may be administered simultaneously or sequentially, as long as they are given in a manner sufficient to allow both agents to achieve effective concentrations in the body.

The term "infertile female" as used herein includes postmenopausal and perimenopausal females past the age of reproduction and younger women not capable of conception, including ovulation, fertilization and implantation.

The term "effective for contraception" as used herein includes sufficient inhibition of fertility, including ovulation or implantation.

The term "contraceptive blood level" as used herein includes a blood level sufficient to inhibit fertility, including ovulation or implantation.

The term "females at high risk of developing ovarian cancer" includes females with a family history of breast or ovarian cancer, females with a prior history of breast or ovarian cancer, or females with a mutation in the BRCA1 gene or any other mutation shown to be associated with a high risk of developing ovarian cancer.

Various combinations of progestin and estrogen that have been used in oral contraceptives are shown in Table 1.

TABLE 1

Previously Used Combinations of Progestin and Estrogen

| Progestin | Dose (mg) | Norethindrone Equivalent Dose | Estrogen | Dose (mg) | EE Equivalent Dose (mg) | P/E Ratio |
|---|---|---|---|---|---|---|
| Norethynodrel | 9.85 | 9.85 | Mestranol | 0.150 | 0.105 | 93.810 |
| | 5.00 | 5.00 | | 0.075 | 0.053 | 95.238 |
| | 2.50 | 2.50 | | 0.036 | 0.025 | 99.206 |
| | 2.50 | 2.50 | | 0.100 | 0.070 | 35.714 |
| Norethindrone | 10.00 | 10.00 | Mestranol | 0.060 | 0.042 | 238.095 |
| | 2.00 | 2.00 | | 0.100 | 0.070 | 28.571 |
| | 1.00 | 1.00 | | 0.050 | 0.035 | 28.571 |
| | 1.00 | 1.00 | | 0.080 | 0.056 | 17.857 |
| Norethindrone | 1.00 | 1.00 | Ethinyl estradiol | 0.050 | 0.050 | 20.000 |
| | 0.50 | 0.50 | | 0.035 | 0.035 | 14.286 |
| | 0.40 | 0.40 | | 0.035 | 0.035 | 11.429 |
| Norethindrone acetate | 2.50 | 2.50 | EE | 0.050 | 0.050 | 50.000 |
| | 1.00 | 1.00 | | 0.050 | 0.050 | 20.000 |
| | 0.60 | 0.60 | | 0.030 | 0.030 | 20.000 |
| | 1.50 | 1.50 | | 0.030 | 0.030 | 50.000 |
| | 1.00 | 1.00 | | 0.020 | 0.020 | 50.000 |
| Ethynodiol diacetate | 1.00 | 1.00 | Mestranol | 0.100 | 0.070 | 14.286 |
| Ethynodiol diacetate | 1.00 | 1.00 | EE | 0.050 | 0.050 | 20.000 |
| dl-Norgestrel | 0.50 | 2.00 | EE | 0.050 | 0.050 | 10.000 |
| | 0.30 | 1.20 | | 0.030 | 0.030 | 10.000 |

Equivalencies
50 mg Mestranol = 35 mg Ethinyl estradiol (EE)
0.5 mg dl-Norgestrel = 2 mg Norethindrone Each block describes a specific combination of progestin and estrogen, e.g., norethynodrel and mestranol, and within each block older combinations are listed first, with successively newer combinations following. Two trends are evident. First, over time the size and ratio of the dosages has decreased, i.e., the downward trend of the progestin component is steeper than the downward trend of the estrogen component. On a relative scale, therefore, estrogen has become more important over time. Second, with this downward trend in dosage, it is apparent that the relative ratio of progestin to estrogen is also trending downward. By contrast, the present invention emphasizes the greater importance of progestin in combination with estrogen, and thus emphasizes combination ratios even higher than those ratios, e.g., 100–1, that have long since been abandoned.

Other aspects and advantages of the present invention will be understood upon consideration of the following illustrative examples. Example 1 addresses the effect of administration of progestin or estrogen products, alone or in combination, on the ovarian epithelial cells of monkeys. Example 2 addresses the effect of progestin in vitro on the ovaries of humans. Example 3 addresses the effect of progestins on apoptosis in the ovarian epithelium of domestic fowl. Example 4 relates to expression of the progesterone receptor in human ovarian tissue. Example 5 relates to a chemoprevention trial in domestic fowl. Example 5 addresses the effect of progestin and estrogen products, alone or in combination, on the ovaries of humans. Example 7 addresses the effect of hormonally active agents, alone or in combination, in vitro on human ovarian tissue. Example 8 addresses the effects of hormonally active agents in vivo on monkey ovaries. Example 9 addresses the effect of various hormonally active agents on the ovarian tissue of transgenic mice that have been altered to have altered expression of receptors, growth factors, integrins or protooncogenes.

EXAMPLE 1

Effect of Estrogen and Progestin In Vivo on Monkey Ovaries

Young female adult cynomolgus monkeys were fed a diet for three years that contained either no hormones, the oral combination contraceptive "Triphasil®," the estrogenic component of "Triphasil®" (ethinyl estradiol) alone, or the progestin component of "Triphasil®" (levonorgestrel) alone, each administered in the same pattern that occurs in a "Triphasil®" regimen. Doses were scaled on the basis of caloric intake, which is the accepted way to achieve human-equivalent doses. The human-equivalent doses were thus: six days of 0.030 mg ethinyl estradiol+0.050 mg levonorgestrel, followed by 5 days of 0.040 mg ethinyl estradiol+0.075 mg levonorgestrel, followed by 10 days of 0.030 mg ethinyl estradiol+0.125 mg levonorgestrel, followed by 7 days of no treatment. This cyclic regimen was repeated every 28 days continuously for 2 years.

At the completion of the two years of the study, the animals were sacrificed, and their ovaries were removed and both formalin fixed and paraffin embedded as well as flash frozen and stored at minus 70 degrees Celsius. Five-micron ovarian sections were mounted on coated slides, and stained with the Apoptag-plus kit (Oncor, Gaithersburg, Md.), which specifically labels the 3' end of free DNA fragments in cells undergoing DNA fragmentation, a characteristic of apoptosis. After staining, cells undergoing apoptosis were easily identified by their dark brown nuclear discoloration. The ovarian surface epithelium was examined histologically to assess ovarian epithelial morphology and to determine the percentage of ovarian cells undergoing apoptosis. To calculate the percentage of ovarian epithelial cells undergoing apoptosis, both the total number of ovarian epithelial cells and the number undergoing apoptosis were counted on each five-micron ovarian section. At each step, the investigators were completely blinded with regard to which treatment group was associated with each ovary.

The ovarian surface epithelium is comprised of a single layer of epithelial cells that rests on a basement membrane overlying the ovarian cortex. In the control and non-progestin treated monkeys, the ovarian surface epithelium typically had a lush appearance with the epithelial cells containing abundant cytoplasm and visible microvilli at the surface with apoptotic cells rarely seen. In the progestin treated monkeys, the ovarian surface epithelium was observed to contain numerous brown-staining apoptotic cells.

The median percentage of ovarian epithelial cells undergoing apoptosis for each of the treatment groups is shown below in Table 2.

TABLE 2

Apoptotic Effect of Four Treatments On Monkey Epithelia

| Treatment | Number | Median Percent of Apoptotic Cell Counts | Range of Percent of Apoptotic Cell Counts |
| --- | --- | --- | --- |
| Control | 20 | 3.8% | 0.1–33.0% |
| Ethinyl-estriadol-only | 20 | 1.8% | 0.1–28.6% |
| Combination Pill | 17 | 14.5% | 3.0–61.0% |
| Levonorgestrel | 18 | 24.9% | 3.5–61.8% |

Multiple Comparisons: Control - Levonorgestrel ($p < 0.001$)
Combination Pill - Ethinyl-estradiol ($p < 0.001$)
Ethinyl-estradiol - Levonorgestrel ($p < 0.001$)
Control - Combination Pin ($p < 0.01$)

From Table 2, the median percentage of apoptosis in the control group of monkeys not receiving any hormonal therapy was approximately 3.8%. Statistically, this was not significantly different from the rate of apoptosis seen in the ovarian epithelium in monkeys receiving only the estrogen component of "Triphasil®," ethinyl estradiol, in which the median percentage of apoptosis was 1.8%.

A marked and significantly greater level of apoptosis was noted in the other two groups of monkeys—those that received the combination pill (containing both ethinyl estradiol and levonorgestrel) and those that received levonorgestrel (the progestin) alone. In this latter group (progestin alone), the observed median percentage of cells undergoing apoptosis was over six times greater than the level of apoptosis observed in the control, untreated monkeys. Because the only difference between the combination pill group and estrogen-alone group is the presence of the levonorgestrel component of the combination pill, and because the degree of apoptosis of the ovarian epithelium in the estrogen-alone group was no different than that of the control group, these data demonstrate that the accelerated rate of apoptosis in the ovarian epithelium in combination pill treated monkeys is due to the effects of the progestational component (levonorgestrel) of the combination pill. Moreover, the higher rate of apoptosis among the monkeys that received a progestational agent alone compared to the monkeys that received the combination pill, although not statistically significant, indicates that progestin-only treatment is more effective at inducing apoptosis of the ovarian surface epithelium than a progestin/estrogen combination treatment.

EXAMPLE 2

Effect of Progestin In Vitro on Human Ovarian Tissue

According to this example, levonorgestrel was found to induce apoptosis in immortalized human ovarian epithelial cells. Specifically, a spontaneously immortalized cell line, M-100, derived from a normal human ovarian epithelial cell culture was plated in 24 well plates at a concentration of 100,000 cells per well. After 24 hours, the wells were treated with either levonorgestrel (20 ng/ml) or control medium, and allowed to incubate for 96 hours. All experiments were performed in triplicate. After 96 hours, cell lysates were extracted from each of the wells, normalized for cell number, and analyzed for DNA-histone complexes indicative of apoptosis using a cell death ELISA (Boehringer Mannheim). A statistically significant (100%) increase in apoptosis was measured in M-100 cells treated with levonorgestrel as compared to controls ($P<0.05$).

In addition, M-100 cells were grown to confluence in 60 millimeter dishes and then treated with levonorgestrel (100 uM) for 12, 24, 48, 72 and 96 hours. Then, cells were harvested, centrifuged at 6000 g for 10 minutes and the resultant pellets were resuspended in 200 ul nuclei lysis buffer (SM guanidine thiocyanate, 25 mM sodium citrate pH 7.0, 100 mM β-mercaptoethanol). DNA was precipitated with an equal volume of isopropanol at $-70°$ C. for one hour. Samples were centrifuged for 30 minutes at 12,000 g at $4°$ C., and the DNA pellets were washed in 70% ethanol at room temperature. Pellets were resuspended in TE buffer and incubated overnight at $37°$ C. with 0.5 mg/ml RNase A (Sigma Chemical Co., St. Louis, MO). Pellets were again resuspended and an optical density reading at 260 nm wavelength was obtained on a Perkin Elmer Lambda 3B UV/vis spectrophotometer to determine the concentration of DNA. Equal amounts of each DNA sample were then subjected to electrophoresis on a horizontal 1.5% agarose gel containing ethidium bromide and visualized under UV illumination. DNA ladders indicative of apoptosis were observed at 48, 72 and 96 hours in M-100 cells treated with levonorgestrel, with no evidence of apoptosis observed in control cultures treated with the appropriate control vehicle solution.

EXAMPLE 3

Apoptosis in Domestic Fowl

According to this example, levonorgestrel was found to induce apoptosis in the ovarian epithelium of domestic fowl. Domestic fowl is the one animal species with a high incidence of spontaneous ovarian carcinoma. Specifically, ovarian epithelial cells from domestic hens were cultured using the scrape method according to the method of Arends et al., Int. Rev. Exp. Pathol 32:223–254 (1991). The avian ovarian epithelial cell cultures were treated with levonorgestrel (100 uM) for 96 hours. DNA was extracted using the method described in example 2 and subjected to electrophoresis. A DNA ladder indicative of apoptosis was observed in avian ovarian epithelial cells treated with progestin, with no effect observed in the control cells.

EXAMPLE 4

Progesterone Receptor Expression in Human Ovaries

According to this example, the expression of progesterone receptor was examined in the normal human ovary. Immunohistochemical staining for progesterone receptor was performed on normal ovarian tissue samples obtained from 40 women who underwent oophorectoiny as part of a gynecologic procedure performed for benign gynecologic indications. The progesterone receptor was found to be uniformly expressed by the ovarian epithelium in all cases, including the ovaries from both pre- and post-menopausal women. In addition, progesterone receptor expression was detected in the ovarian epithelium lining inclusion cysts trapped within the ovarian stroma. Progesterone receptor expression was absent in all non-epithelial areas of the ovary.

EXAMPLE 5

Chemoprevention Trial in Domestic Fowl

According to this example, a chemoprevention trial is carried out in domestic fowl. The domestic fowl has great potential as an animal model for studying chemoprevention of ovarian cancer as it is the only known animal model with a high incidence of spontaneous ovarian adenocarcinoma is the domestic fowl. Fredrickson, Environ Health Perspect 73: 35–51 (1987) reported that in two flocks of hens with initial ages of either two or three years, followed prospectively until ages 3.9 to 4.2 years, there were 33 cases of ovarian adenocarcinoma in 236 chickens. This gives an incidence of 14 percent in the two-year period of observation.

In addition to its known high incidence of ovarian cancer, there are other features of the domestic fowl that make it attractive for studying chemoprevention of ovarian cancer, particularly with progestin agents: (1) The ovulatory cycle in the domestic fowl has been extensively studied and characterized previously, and is highly regulated by gonadotropins, estrogens, androgens and progestin. (2) Under standard conditions, the domestic fowl ovulates on almost a daily basis. However, anovulation can be induced under controlled conditions that include dietary restriction. It has been shown in a long term, one year, study in broiler hens, for example, that dietary restriction to maintain pullet weight (beneath the minimum required to support egg production) causes complete cessation of ovulation. Dunn et al., Poultry Science 71:2090–2098 (1992). Thus, ovulation in the domestic fowl can be carefully controlled, allowing the design of experiments that can test the relative importance of ovulation inhibition versus molecular biologic effects of contraceptives with regard to chemoprevention of ovarian cancer. (3) Expression and regulation of known effectors of apoptosis such as bax, bcl-2, and p53 have been studied extensively in the domestic fowl. (4) The ovarian epithelium in the domestic fowl expresses progestin receptor in both the A and B isoforms. (5) We have been able to induce apoptosis with the progestin levonorgestrel in cultured normal ovarian epithelial cells from the chicken (see the data of Example 3).

According to this example, a two year study in the domestic fowl, is carried out to test the hypothesis that progestin confers chemoprevention against ovarian cancer. In addition, the study will test the hypothesis that the protective effect of progestin is due to a biologic effect independent of ovulation. Because the incidence of ovarian cancer in the domestic hen rises steadily after two years of life, healthy two year-old commercial hens (Gallus Domesticus) will be used. A large flock of commercial chickens currently undergoing a two-year egg-lay test will be available for our planned chemoprevention trial. These hens having been laying eggs almost continuously for two years.

Two thousand healthy two year old commercial hens (Gallus Domesticus) hens are tested according to the example. A baseline necropsy is performed on 400 birds, for the purpose of determining the prevalence of ovarian cancer in our flock at the onset of the study. 1600 hens are then randomized to either of 4 groups: (1) Untreated Control (standard feed), (2) Feed restricted control (feed restriction to maintain pullet weight, but below threshold required for ovulation), (3) Standard feed plus progestin (norgestrel scaled calorically to approximate a human dose of 0.25 mg/day in the feed to achieve 0.125 mg/day of the active isomer, levonorgestrel). This dose equals the highest daily content of levonorgestrel in the Triphasil pills found to have an apoptotic effect on the ovarian epithelium in non-human primates. (4) Feed restriction plus progestin (norgestrel scaled calorically to approximate a human dose of 0.25 mg/day in the feed to achieve 0.125 mg/day of the active isomer, levonorgestrel). In a pilot study with 100 hens, complete cessation of ovulation has been observed in those hens that have been diet restricted, and that the daily dose of norgestrel used according to this example no anovulatory effect in chickens. Therefore, it is expected that the ovulatory rate in groups one and three to be similar, and for hens in groups two and four to be anovulatory.

Animal care, poultry house ventilation and temperature control will be controlled. Investigators will be blinded with regard to which birds belong to which treatment group. Bird identification will be maintained by wing band. Any birds who become symptomatic, and all remaining birds at the end of the two years of the trial will undergo euthanasia, and a pathologic evaluation will be performed to identify those birds in each group which have developed ovarian cancer during the study period. In addition, a careful histologic and immunohistochemical examination of the ovarian epithelium will be performed on a randomly selected subset of 30 birds from each group at the end of the study to assess the apoptotic effect of progestin treatment on the ovarian epithelium. Methods used for assessing apoptosis will be according to those reported in example 1 and the primary outcome to be measured is to be time of onset and incidence of ovarian adenocarcinomas. Secondary outcomes will be apoptotic effect of progestin on the ovarian epithelium.

EXAMPLE 6

Effect of Progestin and Estrogen In Vivo on Human Ovaries

Various progestins alone, including pregnanes, estranes and gonanes, various estrogens alone, or various progestin-estrogen combinations at varying doses are administered to women for at least one month prior to a scheduled surgery for removal of the ovaries and uterus. In particular, regimens of estrogen alone, estrogen with medroxyprogesterone acetate (or another 17-hydroxy-progesterone derivative), and estrogen with levonorgestrel (or another 19-nortestosterone derivative) are evaluated. To evaluate the effects of the different dosage regimens, the ovaries are examined for various markers, including apoptosis, proliferation, expression of growth factors, expression of steroid hormone receptors, and expression of other enzymes or genes.

EXAMPLE 7

Effect of Hormonally Active Agents In Vitro on Human Ovarian Tissue

Ovarian epithelia cultured from ovaries removed from normal women or women with epithelial ovarian cancer are treated with various progestins alone, including pregnanes, estranes and gonanes, various estrogens alone, various progestin-estrogen combinations, progesterone receptor agonists, progesterone receptor antagonists, estrogen receptor agonists, or estrogen receptor antagonists, each at varying doses and varying durations, from e.g., 24 hours to 7 days. The ovarian tissue is then examined for various markers, including apoptosis, proliferation, expression of growth factors, expression of steroid hormone receptors, and expression of other enzymes or genes. The most potent agent for inducing apoptosis is determined.

EXAMPLE 8

Effect of Hormonally Active Agents In Vivo on Monkey Ovaries

Mature young female monkeys are treated with one of the following: control, leuprolide acetate (a gonadotropin releasing hormone [GnRH or LHRH]agonist), various oral contraceptives, levonorgestrel, norethindrone, medroxyprogesterone acetate, ethinyl estradiol, testosterone, testosterone derivatives, RU-486, progestin agonists, progestin antagonists, estrogen agonists and estrogen antagonists, each at varying doses. The ovarian tissue is removed and examined for various markers, including apoptosis, proliferation, expression of growth factors, expression of steroid hormone receptors, and expression of other enzymes or genes.

EXAMPLE 9

Effect of Hormonally Active Agents In Vivo on Ovaries of Transgenic Mice

The apoptotic effect of various progestins, estrogens or androgens, each at varying doses, is evaluated on the ovarian tissue of transgenic mice or Domestic hens that have been altered to "knockout" their progestin receptor, to have an altered expression of the estrogen receptor, to express BRCA1, or to have altered expression of growth factors, integrins or protooncogenes.

Numerous modifications and variations in the practice of the invention are expected to occur to those skilled in the art upon consideration of the foregoing description on the presently preferred embodiments thereof. Consequently the only limitations which should be placed upon the scope of the present invention are those that appear in the appended claims.

What is claimed is:

1. A method of preventing ovarian cancer comprising administering to a female subject in need thereof a multiphase regimen comprising a first phase in which an estradiol estrogen product is administered in combination with a 19-nortestosterone progestin product; and a second phase in which an estradiol estrogen product is administered in combination with a 19-nortestosterone progestin product; and a third phase in which a 19-nortestosterone progestin product is not administered; and wherein said first phase is greater than 30 days and wherein the 19-nortestosterone progestin product administered in said second phase is characterized by at least twice the effective dosage of the 19-nortestosterone progestini product administered in said first phase, wherein the results obtained produce an enhanced effect.

2. The method of claim 1 wherein said first phase is greater than 60 days.

3. The method of claim 1 wherein said first phase is greater than 90 days.

4. A method of preventing ovarian cancer comprising administering to a female subject in need thereof a multiphase regimen comprising a first phase in which an estradiol estrogen product is administered; a second phase in which an estradiol estrogen product is administered in combination with a 19-nortestosterone progestin product; and wherein said first phase is greater than 30 days and wherein the 19-nortestosterone progestin product administered in said second phase is characterized by a dosage less than sufficient to prevent ovulation, wherein the results obtained produce an enhanced effect.

5. The method of claim 4 wherein after said second phase there is a third phase in which a progestin product is not administered.

6. The method of claim 5 wherein said first phase is greater than 60 days.

7. The method of claim 5 wherein said first phase is greater than 90 days.

8. A method of preventing ovarian cancer comprising administering to a female subject in need thereof a multiphase regimen comprising a first phase in which an estradiol estrogen product is administered; a second phase in which an estradiol estrogen product is administered in combination with a 19-nortestosterone progestin product; and wherein said first phase is greater than 30 days and wherein the estradiol estrogen product administered in said first phase is characterized by a dosage less than sufficient to prevent ovulation, wherein the results obtained produced an enhanced effect.

9. A method of preventing ovarian cancer comprising administering to a female subject in need thereof a multiphase regimen comprising a first phase in which an estradiol estrogen product is administered in combination with a 19-nortestosterone progestin product; a second phase in which an estradiol estrogen product is administered in combination with a 19-nortestosterone progestin product wherein the estradiol estrogen product is administered at a lower effective dosage than in said first phase; and a third phase in which an estradiol estrogen product is administered with a 19-nortestosterone progestin product wherein the 19-nortestosterone progestin product is administered at a higher effective dosage than in said first and second phases, wherein the results obtained produce an enhanced effect.

10. The method of claim 9 wherein the multiphase regimen has no breaks in hormone administration which would result in breakthrough bleeding.

11. The method of claim 9 wherein at least one of said phases is greater than 14 days.

12. The method of claim 11 wherein said at least one of said phases is greater than 21 days.

13. A method of preventing ovarian cancer comprising administering to a female subject in need thereof a multiphase sequence of pharmaceutical dosages comprising a first series of dosages comprising an estradiol estrogen product and a 19-nortestosterone progestin product; and a second series of dosages comprising an estradiol estrogen product and a 19-nortestosterone progestin product wherein the first series of dosages is administered for greater than 30 days and said 19-nortestosterone progestin product in said second series is characterized by at least twice the effective dosage of the 19-nortestosterone progestin product in said first series, wherein the results obtained produce an enhanced effect.

14. The method of claim 13 which comprises administering a third series of dosages which are a placebo.

15. The method of claim 13 wherein said progestin product is levonorgestrel and wherein said estrogen product is estradiol.

16. A method of preventing ovarian cancer comprising administering to a female subject in need thereof a multiphase sequence of pharmaceutical dosages comprising a first series of dosages comprising an estradiol estrogen produce; and a second series of dosages comprising an estradiol estrogen product and a 19-nortestosterone progestin product wherein the first series of dosages is administered for greater than 30 days and wherein the 19-nortestosterone progestin product in said second series is characterized by a dosage less than sufficient to prevent ovulation, and wherein the results obtained produce an enhanced effect.

17. A method of preventing ovarian cancer comprising administering to a female subject in need thereof a multiphase sequence of pharmaceutical dosages comprising a first series of dosages comprising an estradiol estrogen product and a 19-nortestosterone progestin product; a second series of dosages comprising an estradiol estrogen product and a 19-nortestosterone progestin product wherein said estrogen product is administered at a lower effective dosage than in said first series; and a third series of dosages comprising a 19-nortestosterone progestin product and an estradiol estrogen product wherein said 19-nortestosterone progestin product is administered at a higher effective dosage than in said first series, and wherein the results obtained produce an enhanced effect.

18. The regimen of claim 17 wherein at least one of said phases is greater than 14 days.

19. The method of claim 18 wherein said at least one of said phases is greater than 21 days.

* * * * *